United States Patent [19]

Ploog et al.

[11] Patent Number: 4,833,253

[45] Date of Patent: May 23, 1989

[54] PROCESS FOR THE PRODUCTION OF LOW-VISCOSITY AMPHOTERIC SURFACTANTS

[75] Inventors: Uwe Ploog, Haan; Guenter Uphues, Monheim; Peter Nikolaus, Hilden, all of Fed. Rep. of Germany

[73] Assignee: Henkel Kommanditgesellschaft auf Aktien, Duesseldorf, Fed. Rep. of Germany

[21] Appl. No.: 129,276

[22] Filed: Dec. 7, 1987

[30] Foreign Application Priority Data

Dec. 8, 1986 [DE] Fed. Rep. of Germany ....... 3641871

[51] Int. Cl.$^4$ .......................................... C07D 233/04
[52] U.S. Cl. .................... 548/352; 548/353; 548/354
[58] Field of Search ................ 548/352, 353, 354

[56] References Cited

U.S. PATENT DOCUMENTS

| 2,528,378 | 10/1950 | McCabe et al. | 260/309.6 |
| 2,773,068 | 12/1956 | Mannheimer | 260/309.6 |
| 3,555,041 | 1/1971 | Katz et al. | 532/861 |
| 4,059,488 | 11/1977 | Wakeman et al. | 252/542 |
| 4,212,983 | 7/1980 | Phillips et al. | 548/352 |
| 4,269,730 | 5/1981 | Wechsler et al. | 252/356 |
| 4,304,932 | 12/1981 | Phillips et al. | 562/561 |

FOREIGN PATENT DOCUMENTS

| 0040346 | 11/1984 | European Pat. Off. | 548/351 |
| 0850514 | 5/1960 | United Kingdom | 548/351 |
| 0930296 | 3/1963 | United Kingdom | 548/351 |
| 1352770 | 8/1974 | United Kingdom | 548/351 |

*Primary Examiner*—Mary C. Lee
*Assistant Examiner*—J. Richter
*Attorney, Agent, or Firm*—Ernest G. Szoke; Wayne C. Jaeschke; Real J. Grandmaison

[57] ABSTRACT

Low viscosity amphoteric surfactants are prepared by quaternization of low diamine content imidazolines by a process in which certain addition and temperature parameters are strictly observed. Imidazolines suitable as a starting material may be obtained by heating fatty acids and aminoethanolamine in an inert solvent until water is eliminated, removing the water formed from the reaction mixture by azeotropic distillation and, finally, distilling off the solvent and the residual amine.

20 Claims, No Drawings

PROCESS FOR THE PRODUCTION OF LOW-VISCOSITY AMPHOTERIC SURFACTANTS

BACKGROUND OF THE INVENTION

1. Field of the Invention

This invention relates to a process for the production of low diamide content imidazolines, and their reaction with a quaternizing agent to form low-viscosity amphoteric surfactants.

2. Discussion of Related Art

U.S. Pat. No. 4,212,983 describes the production of a low diamide content imidazoline by heating of a crude imidazoline with an excess of aminoethyl ethanolamide through treatment of the reaction mixture in vacuo under reflux conditions.

The production of imidazoline-acrylate adducts is described in U.S. Pat. No. 3,555,041. The corresponding starting imidazolines are prepared by azeotropic reaction of fatty acid and amine.

U.S. Pat. No. 4,058,488 describes the production of imidazoline oxides, the starting imidazolines being prepared, inter alia, by azeotropic reaction. The corresponding amphoteric surfactants may be obtained from the imidazolines by reaction with a quaternizing agent.

U.S. Pat. No. 2,528,378 describes the reaction of equimolar quantities of imidazoline and chloroacetic acid in an aqueous solution of excess alkali. A solid mass is obtained.

Solid products are also obtained in accordance with U.S. Pat. No. 2,773,068, wherein an alkaline sodium chloroacetate solution is initially introduced into a reactor and imidazoline subsequently reacted with chloroacetic acid in the presence of an excess of sodium hydroxide, the chloroacetic acid being used in a two-fold excess.

Great Britain Pat. No. 850,514 describes the hydrolysis of imidazoline to the linear aminoamide which is reacted with sodium chloroacetate and mixed with ether sulfate. The specification thus describes the reaction of hydrolyzed imidazoline with sodium chloroacetate.

Products containing a high proportion of free chloroacetic acid are described in German patent application No. 20 63 424, equivalent to Great Britain Pat. No. 1,352,770. Imidazoline and chloroacetic acid are initially introduced, followed by the addition of sodium hydroxide at elevated temperature and at substantially neutral pH value.

Great Britain Pat. No. 930 296 describes the reaction of equimolar quantities of imidazoline and chloroacetic acid which is neutralized with a slight excess of sodium hydroxide. This reaction is carried out at 0° to 15° C. After heating to 95° C., more sodium hydroxide is added. The reaction takes place in the presence of excess sodium hydroxide, giving carboxymethylation products based on a linear and branched aminoamide. The very low temperature at the beginning of the reaction is said to reduce the effect of the excess of sodium hydroxide on the ring cleavage.

European Pat. No. 1 006 describes the reaction of an imidazoline at 40° to 90° C. and at a pH of 7 to 11.5. When 0.5 mole of carboxymethylation substance has reacted, the pH value is raised to between 9 and 12. The reaction is controlled in accordance with the following general formula:

$$\text{pH max.} = [200 - \text{temp.}(°C.)]/13$$

This complicated process gives products containing more than 1% of free chloroacetic acid.

U.S. Pat. No. 4,269,730 in column 1 describes the reaction of imidazoline with neutralizing chloroacetic acid in the absence of strong alkali. In column 2, reference is made to the need to adhere strictly to the sequence, i.e. first reaction without alkali, then addition of alkali. According to the claims therein, 1 mole of imidazoline is heated at 70° to 80° C. with at least 1 mole of sodium chloroacetate in water (solids content 20 to 50%) until almost all the sodium chloroacetate has been consumed, after which an equivalent quantity of sodium hydroxide is added and the reaction mixture subsequently heated to 70° to 80° C. until the ring-opening reaction has started. Imidazoline and chloroacetate are reacted with one another in an elaborate, carefully controlled process in such a way that sodium chloroacetate is always present in excess. According to column 13 therein, the process requires a 92 to 99.5% imidazoline which is substantially free from starting methyl ester (0 to 2%) and which may only contain up to 5% aminoamide ("monoamide"); diamide contents are not mentioned.

European Pat. No. 40 346 describes a process for elimination of the diamine formed with the imidazoline which produces particularly persistant clouding in the final amphoteric surfactant. To destroy the diamide, the imidazoline is treated with an alkali before the reaction with sodium chloroacetate and is thus specifically converted into linear aminoamide. The resulting amphoteric surfactant is free from clouding, but is highly viscous.

An object of the present invention is to provide a new process for the production of highly concentrated, low-viscosity amphoteric surfactants which do not have any of the disadvantages mentioned above. This object is achieved by a quaternization process which starts out from low diamide content imidazolines and in which certain addition and temperature parameters are strictly observed.

DESCRIPTION OF THE INVENTION

Other than in the operating examples, or where otherwise indicated, all numbers expressing quantities of ingredients or reaction conditions used herein are to be understood as modified in all instances by the term "about".

The present invention relates to a process for the production of low-viscosity amphoteric surfactants by quaternization of low diamide content imidazolines comprising;

(a) adding 1 mole of imidazolines containing at least 80%/wt. of imidazoline and at most 3%/wt. of diamide to from 1 to 3 moles of a neutralized quaternizing agent dissolved in water, (b) adding said imidazoline at an increasing rate to the quaternizing agent solution which is heated to between 55° and 65° C. over a period of at least one hour while maintaining said temperature range, (c) maintaining the temperature of the solution at between 55° and 65° C. for between 80 and 100 minutes after said imidazoline has been added to the quaternizing agent solution, (d) increasing the temperature of the solution to between 75° and 85° C. for between 80 and 100 minutes, with the proviso that said imidazoline has reacted with said quaternizing agent in a molar ratio of about 1:1, (e) adding to the solution 1 mole equivalent of an alkali metal hydroxide, based on the quantity of quaternizing agent initially used, over a period of at most about 15 minutes at a solution temperature of at least 80° C. to adjust the pH to a value of from 11.5 to 12.0, and (f) on completion of the alkali metal hydroxide addition, keeping the reaction mixture at a temperature of between 80° and 90° C. for a period of 140 to 180 minutes.

It is preferred that from about 1.5 to about 2.5 moles of neutralized quaternizing agent dissolved in water be employed as the starting solution for step (a) above.

Halocarboxylic acids containing 2 or 3 carbon atoms and alkali metal salts thereof may be used as the quaternizing agent. Sodium chloroacetate is a preferred quaternizing agent.

Potassium hydroxide and sodium hydroxide are preferred alkali metal hydroxides. Sodium hydroxide in the form of a 50%/wt aqueous solution is particularly suitable.

According to the invention, the quaternizing agent used for ring-opening of the low-diamide content imidazolines is initially introduced in fully neutralized form. The pH value is not controlled by the addition of NaOH in the first step, instead the imidazoline is added in portions and, after addition of the imidazoline, the pH value is allowed to fall to a value below 7. During addition of the NaOH, the temperature is allowed to rise to almost 100° C.

The technical grade imidazolines containing at least 80%/wt imidazoline and at most 3% by weight diamide which are required as starting material for carrying out the process according to the invention as described above may be prepared by a new process comprising the condensation of fatty acids with aminoethyl ethanolamine under special conditions. This new process comprises;

(a) heating 1 mole of a $C_6$–$C_{22}$ fatty acid while stirring with an equimolar quantity or up to a 0.3 molar excess of aminoethyl ethanolamine in the presence of 0.05 to 0.1%/wt of hydrophosphorous acid, based on the mixture as a whole, in an inert solvent forming an azeotropic mixture with water until water is eliminated, (b) separating the water formed from the reaction mixture by zeotropic distillation, and (c) after the separation of water is complete, distilling off the solvent under reduced pressure along with the residual amine.

In the preparation of the technical grade imidazoline, suitable fatty acids include, for example, lauric acid, caproic acid, caprylic acid, capric acid, myristic acid, palmitic acid, stearic acid, arachic acid, behenic acid, oleic acid, erucic acid, isononanoic acid, isotridecanoic acid, isostearic acid, 12-hydroxystearic acid, and mixtures thereof.

The preferred solvent is xylene, although other solvents which form an azeotrope with water may also be used.

The advantages of this process lie in the fact that a low diamide content imidazoline containing less than 1%/wt diamide is surprisingly obtained by closure of the imidazoline ring under the conditions of an azeotropic distillation. In conventional processes carried out in the absence of a solvent, diamide contents of approximately 8% are obtained, even with a 50% excess of amine.

The following examples describe preferred embodiments of the process according to the invention for the production of low diamide content imidazolines as intermediate products and their reaction with a quaternizing agent to form low viscosity amphoteric surfactants. The amphoteric surfactants thus obtained contain only minute amounts of residual quaterizing agent. When chloroacetic acid is used, the remaining quaterizing agent amounts to less than about 0.2% by wt.

As employed herein, the term low viscosity means that the viscosity of the amphoteric surfactant in relation to an aqueous solution having a solid content of 50% by wt. is less than about 5000 centipoise, preferably between about 100 and about 2000 centipoise at 20° C. as determined by the Höppler method (DIN 53015).

EXAMPLE I

This example describes the production of a low diamide content imidazoline.

2000 g (10 moles) of 99%/wt lauric acid and 1300 g (12.5 moles) of aminoethyl ethanolamine were heated with stirring under nitrogen in the presence of 3.3 g of hypophosphorous acid (50%) in approx. 300 ml of xylene until water was eliminated. While the temperature was slowly increased (regulated through the xylene content) from 159° to 209° C., 442.7 g of an aqueous distillate containing approx. 104 g (approx. 1 mole) of amine distilled over in 4 hours. After the elimination of water had stopped, the solvent was distilled off with the residue amine under a vacuum of 25 mbar.

Characteristic data of the product: $N_{Kj}=10.3\%$; $N_{titr}=5.22\%$.

Imidazoline content: approx. 99% (as determined by UV spectroscopy).

Diamide content: 1.07% (as determined by passage over an ion exchanger).

EXAMPLE II 108 g of sodium chloroacetate were introduced into 220 g of water. The temperature of the solution was slowly increased to 60° C. over a period of 20 minutes and 98 g of the imidazoline prepared in accordance with Example I was added thereto at such a rate that 25% of it had been added after 30 minutes and the total quantity after 65 minutes. The reaction mixture was then stirred for 90 minutes at the same temperature and then for 120 minutes at 80° C. 1 mole-equivalent, based on the quantity of sodium chloroacetate, of sodium hydroxide in the form of a 50% aqueous solution was then added over a period of 10 minutes, so that a pH value of 11 was reached. The temperature of the reaction mixture was then kept at 80° to 90° C. for another 120 minutes, followed by cooling.

A low-viscosity solution having a solids content of approx. 45% was obtained.

Characteristic data of the product: $N_{Kj}=2\%$; Chloroacetic acid=0.05%; Viscosity: 220 centipoise; Imidazoline content=0%.

EXAMPLE III 224 g of an imidazoline prepared in accordance with Example I from coconut oil fatty acid were added to a solution of 389 g of water and 234 g of sodium chloroacetate preheated to 60° C. at such a rate that 20% had been added after 30 minutes, 70% after 60 minutes and the total quantity after 70 minutes. The reaction mixture was then stirred for another 90 minutes at 60° C. and for 90 minutes at 80° C. After the addition of 160 g of 50% sodium hydroxide in 15 minutes, during which the temperature rose to 99° C., the reaction was terminated after another 120 minutes at 80° to 85° C.

A medium-viscosity liquid having a solids content of 50% was obtained.

Characteristic data of the product: $N_{Kj}$=2.2%; Chloroacetic acid=0.1%; Viscosity: 180 centipoise; Imidazoline content=0%.

COMPARISON EXAMPLE I (Preparation per European Pat. No. 1 006)

86 g of chloroacetic acid were dissolved in 180 g of water. 98 g of an imidazoline prepared in accordance with Example I were added at a temperature of 35° C., the temperature rising to 45° C. and the pH value settling at 2.67. The pH value was increased to 11.2 by the addition over a period of 65 minutes of a total of 72.6 g of 50% sodium hydroxide. At the same time, the temperature was increased to 55° C. The pH value was kept at 10.5 to 11.5 for another 145 minutes at 55° C. by the continuous addition of sodium hydroxide. 33.4 g of the 50% sodium hydroxide solution were required for this purpose. The temperature was then increased to 70° C. and a pH value of 11.5 to 12.4 was maintained for another 200 minutes by the addition of a total of 30.6 g of 50% sodium hydroxide. The reaction mixture was then stirred for 60 minutes at 80° C., the pH value falling to 10.5.

A viscous liquid having a solids content of 45% was obtained.

Characteristic data of the product: $N_{Kj}$=1.97%; Chloroacetic acid-1.0%.

COMPARISON EXAMPLE II (Prepration per German patent application No. 20 63 424)

86 g of chloroacetic acid were introduced into 170 g of water, and 98 g of an imidazoline prepared in accordance with Example I was added thereto over a period of 23 minutes during which the temperature rose from 14° to 38° C. The pH value was adjusted to 7.0–7.5 by the addition of 50% aqueous NaOH, the temperature remaining constant at 55° C. for 315 minutes. After the remainder of a total of 109 g of NaOH had been added over a period of 10 minutes, the temperature rose to 65° C. and the pH value to 12.7. The pH value of the solution fell rapidly to 7.5 over a period of another 15 minutes, a sample temporarily becoming gel-like and, soon afterwards, liquid and clear. The mixture was then kept at 80° C. for another 100 minutes, followed by the addition of 9.4 g of hexylene glycol. After cooling, 92% of the end product could be obtained (loss through sampling).

Characteristic data of the product: $N_{Kj}$=2.13%; Chloroacetic acid=3.5%.

We claim:

1. A process for the production of a low viscosity amphoteric surfactant by quaternization of a low diamide content imidazoline comprising;
   (a) adding 1 mole of imidazoline containing at least 80%/wt. of imidazoline and at most 3%/wt. of diamide to form 1 to 3 moles of a neutralized quaternizing agent dissolved in water,
   (b) adding said imidazoline at an increasing rate to the quaternizing agent solution which is heated to between 55° and 65° C. over a period of at least one hour while maintaining said temperature range,
   (c) maintaining the temperature of the solution at between 55° and 65° C. for between 80 and 100 minutes after said imidazoline has been added to the quaternizing agent solution,
   (d) increasing the temperature of the solution to between 75° and 85° C. for between 80 and 100 minutes, with the proviso that said imidazoline has reacted with said quaternizing agent in a molar ratio of about 1:1,
   (e) adding to the solution 1 mole equivalent of an alkali metal hydroxide, based on the quantity of quaternizing agent initially used, over a period of at most about 15 minutes at a solution temperature of at least 80° C. to adjust the pH to a value of from 11.5 to 12.0, and
   (f) on completion of the alkali metal hydroxide addition, keeping the reaction mixture at a temperature of between 80° and 90° C. for a period of 140 to 180 minutes.

2. A process as in claim 1 wherein from about 1.5 to about 2.5 moles of said neutralized quaternizing agent is employed in step (a).

3. A process as claim 1 wherein said quaternizing agent comprises a halocarboxylic acid containing 2 or 3 carbon atoms or the alkali metal salts thereof.

4. A process as in claim 1 wherein said quaternizing agent comprises sodium chloroacetate.

5. A process as in claim 1 wherein said alkali metal hydroxide is selected from potassium hydroxide and sodium hydroxide.

6. A process as in claim 5 wherein said alkali metal hydroxide is in the form of a 50%/wt aqueous solution.

7. A process as in claim 1 wherein sad amphoteric surfactant has a viscosity of less than about 5000 centipoise at 20° C. as determined by the Höppler method (DIN 53 015).

8. A process as in claim 1 wherein said imidazoline has a diamide content of less than about 1%/wt, based on the weight of said imidazoline.

9. A process as in claim 1 wherein said imidazoline is obtained by the steps comprising;
   (a) heating 1 mole of a $C_6$–$C_{22}$ fatty acid while stirring with an equimolar quantity or up to a 0.3 molar excess of aminoethyl ethanolamine in the presence of 0.05 1 to 0.1%/wt of hydrophosphorous acid, based on the mixture as a whole, in an inert solvent forming an azeotropic mixture with water until water is eliminated,
   (b) separating the water formed from the reaction mixture by azeotropic distillation, and
   (c) distilling off the solvent with the residual amine under reduced pressure after the separation of water is complete.

10. A process as in claim 9 wherein said fatty acid is selected from lauric acid, caproic acid, caprylic acid, capric acid, myristic acid, palmitic acid, stearic acid, arachic acid, behenic acid, oleic acid, erucic acid, isononanoic acid, isotridecanoic acid, isostearic acid, 12-hydroxystearic acid, and mixtures thereof.

11. A process as in claim 9 wherein said inert solvent is xylene.

12. A process for the production of a low viscosity amphoteric surfactant by quaternization of a low diamide content imidazoline comprising;
   (a) heating 1 mole of a $C_6$–$C_{22}$ fatty acid while stirring with an equimolar quantity or up to a 0.3 molar excess of aminoethyl ethanolamine in the presence of 0.05 to 0.1%/wt of hydrophosphorous acid, based on the mixture as a whole, in an inert solvent forming an azeotropic mixture with water until water is eliminated, (b) separating the water formed from the reaction mixture by azeotropic distillation, (c) distilling off the solvent with the residual amine under reduced pressure after the separation of water is complete, (d) adding 1 mole of the imidazoline produced containing at least 80%/wt. of imidazoline and at most 3%/wt. of diamide to from 1 to 3 moles of a neutralized quaternizing agent dissolved in water, (e) adding said imidazoline at an increasing rate to the quaternizing agent solution which is heated to between 55° and 65° C. over a period of at least one hour while maintaining said temperature range, (f) maintaining the temperature of the solution at between 55° and 65° C. for between 80 and 100 minutes after said imidazoline has been added to the quaternizing agent solution, (g) increasing the temperature of the solution to between 75° and 85° C. for between 80 and 100 minutes, with the proviso that said imidazoline has reacted with said quaternizing agent in a molar ratio of about 1:1, (h) adding to the solution 1 mole equivalent of an alkali metal hydroxide, based on the quantity of quaternizing agent initially used, over a period of at most about 15 minutes at a solution temperature of at least 80° C. to adjust the pH to a value of from 11.5 to 12.0, and (g) on completion of the alkali metal hydroxide addition, keeping the reaction mixture at a temperature of between 80° and 90° C. for a period of 140 to 180 minutes.

13. A process as in claim 12 wherein from about 1.5 to about 2.5 mole of said neutralized quaternizing agent is employed in step (d).

14. A process as in claim 12 wherein said quaternizing agent comprises a halocarboxylic acid containing 2 or 3 carbon atoms or the alkali metal salts thereof.

15. A process as in claim 12 wherein said quaternizing agent comprises sodium chloroacetate.

16. A process as in claim 12 wherein said alkali metal hydroxide is selected from potassium hydroxide and sodium hydroxide.

17. A process as in claim 16 wherein said alkali metal hydroxide is in the form of a 50%/wt aqueous solution.

18. A process as in claim 12 wherein said amphoteric surfactant has a viscosity of less than about 5000 centipoise at 20° C. as determined by the Höppler method (DIN 53 015).

19. A process in claim 12 wherein said imidazoline has a diamide content of less than about 1%/wt, based on the weight of said imidazoline.

20. A process as in claim 12 wherein said fatty acid is selected from lauric acid, caproic acid, caprylic acid, capric acid, myristic acid, palmitic acid, stearic acid, arachic acid, behenic acid, oleic acid, erucic acid, isononanoic acid, isotridecanoic acid, isostearic acid, 12-hydroxystearic acid, and mixtures thereof.

* * * * *